United States Patent
Cottens et al.

[11] Patent Number: 5,912,253
[45] Date of Patent: Jun. 15, 1999

[54] RAPAMYCIN DERIVATIVES

[75] Inventors: Sylvain Cottens, Witterswil; Richard Sedrani, Basel, both of Switzerland

[73] Assignee: Novartis AG, Basel, Switzerland

[21] Appl. No.: 08/663,169

[22] PCT Filed: Dec. 16, 1994

[86] PCT No.: PCT/EP94/04191

§ 371 Date: Jun. 14, 1996

§ 102(e) Date: Jun. 14, 1996

[87] PCT Pub. No.: WO95/16691

PCT Pub. Date: Jun. 22, 1995

[30] Foreign Application Priority Data

Dec. 17, 1993 [GB] United Kingdom ............... 9325800
Dec. 17, 1993 [GB] United Kingdom ............... 9325802
Apr. 11, 1994 [GB] United Kingdom ............... 9407138
Nov. 1, 1994 [GB] United Kingdom ............... 9421982

[51] Int. Cl.$^6$ ............ A61K 31/395; C07D 498/18
[52] U.S. Cl. ........................... 514/291; 540/456
[58] Field of Search ............... 540/456; 514/291

[56] References Cited

U.S. PATENT DOCUMENTS

| | | |
|---|---|---|
| 5,100,883 | 3/1992 | Schiehser ............... 540/456 |
| 5,118,677 | 6/1992 | Caufield ............... 540/456 |
| 5,118,678 | 6/1992 | Kao et al. ............... 540/456 |
| 5,126,842 | 6/1992 | Failli et al. ............... 540/456 |
| 5,151,413 | 9/1992 | Caufield ............... 540/456 |
| 5,221,670 | 6/1993 | Caufield ............... 540/456 |
| 5,256,790 | 10/1993 | Nelson ............... 514/291 |
| 5,258,389 | 11/1993 | Goulet et al. ............... 540/456 |
| 5,262,423 | 11/1993 | Kao ............... 540/456 |
| 5,310,901 | 5/1994 | Parsons et al. ............... 540/456 |
| 5,310,903 | 5/1994 | Goulet et al. ............... 540/456 |
| 5,527,907 | 6/1996 | Or et al. ............... 540/456 |
| 5,583,139 | 12/1996 | Or et al. ............... 514/291 |
| 5,672,605 | 9/1997 | Or et al. ............... 514/291 |
| 5,728,710 | 3/1998 | Luengo ............... 514/291 |

FOREIGN PATENT DOCUMENTS

| | | | |
|---|---|---|---|
| WO9205179 | 4/1992 | WIPO ............... | 540/456 |
| 9402136 | 2/1994 | WIPO . | |
| WO9409010 | 4/1994 | WIPO ............... | 540/456 |
| 9514023 | 5/1995 | WIPO . | |

*Primary Examiner*—Richard L. Raymond
*Attorney, Agent, or Firm*—Diane E. Furman

[57] ABSTRACT

Novel demethoxy derivatives of rapamycin are found to have pharmaceutical utility, particularly as an immunosuppressants.

19 Claims, No Drawings

RAPAMYCIN DERIVATIVES

This application is a 371 of PCT/EP94/04191, filed Dec. 16, 1994.

This invention comprises novel demethoxy derivatives of rapamycin, such derivatives having pharmaceutical utility, especially as immunosuppressants.

Rapamycin is a known macrolide antibiotic produced by *Streptomyces hygroscopicus*, having the structure depicted in Formula A:

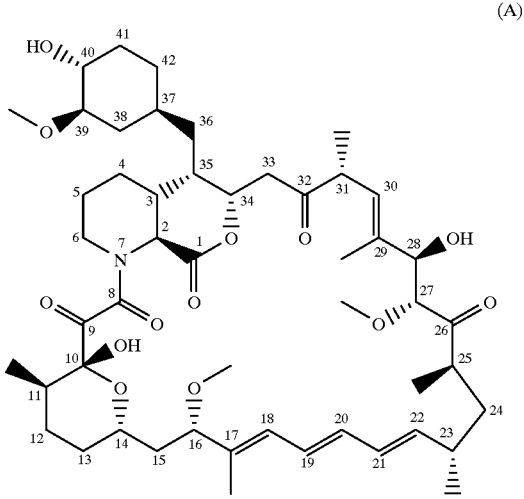

(A)

See, e.g., McAlpine, J. B., et al., J. Antibiotics (1991) 44: 688; Schreiber, S. L., et al., J. Am. Chem. Soc. (1991) 113: 7433; U.S. Pat. No. 3,929,992. (There have been various numbering schemes proposed for rapamycin. To avoid confusion, when specific rapamycin derivatives are named herein, the names are given with reference to rapamycin using the numbering scheme of formula A.) Rapamycin is an extremely potent immunosuppressant and has also been shown to have antitumor and antifungal activity. Its utility as a pharmaceutical, however, is restricted by its very low and variable bioavailability as well as its high toxicity. Moreover, rapamycin is highly insoluble, making it difficult to formulate stable galenic compositions. Numerous derivatives of rapamycin are known. Certain 16-O-substituted rapamycins are disclosed in WO 94/02136, the contents of which are incorporated herein by reference. 40-O-substituted rapamycins are described in, e.g., in U.S. Pat. No. 5,258,389 and PCT/EP 93/02604 (O-aryl and O-alkyl rapamycins); WO 92/05179 (carboxylic acid esters), U.S. Pat. No. 5,118,677 (amide esters), U.S. Pat. No. 5,118,678 (carbamates), U.S. Pat. No. 5,100,883 (fluorinated esters), U.S. Pat. No. 5,151,413 (acetals), and U.S. Pat. No. 5,120,842 (silyl ethers), all of which are incorporated herein by reference. 32-O-dihydro or substituted rapamycin are described, e.g., in U.S. Pat. No. 5,256,790, incorporated herein by reference.

It has now surprisingly been discovered that certain novel demethoxy derivatives of rapamycin (the Novel Compounds) have an improved pharmacological profile over rapamycin, exhibit greater stability and bioavailability, allow for greater ease in producing galenic formulations, and are more potent immunosuppressants. The Novel Compounds comprise rapamycins wherein the methoxy group(s) at position 16 and/or position 39 of rapamycin is deleted and replaced with a selected substituent. Without intending to be bound by any particular theory, we have hypothesized that these particular methoxy groups on rapamycin are targets for metabolic attack and can be replaced with particular selected substituents, optionally in combination with certain further modifications to the molecule, so that activity is retained, or even in some cases, enhanced, and at the same time, susceptibility to metabolic attack is reduced.

The Novel Compounds particularly include rapamycins (i) wherein the methoxy group at the 16 position is replaced with another substituent, preferably (optionally hydroxy-substituted) alkynyloxy, and/or (ii) wherein the methoxy group at the 39 position is deleted together with the 39 carbon so that the cyclohexyl ring of rapamycin becomes a cyclopentyl ring lacking the 39 position methoxy group (i.e., 39-demethoxy-40-desoxy-39-substituted-42-nor-rapamycins, sometimes referred to herein simply as cyclopentyl rapamycins). The remainder of the molecule is as for rapamycin or its immunosuppressive derivatives and analogues, e.g., as described above. Optionally, the molecule is further modified, e.g., such that the hydroxy at the 40-position of rapamycin is alkylated, and/or the 32-carbonyl is reduced.

Preferably, the Novel Compounds are those having the structure of Formula I:

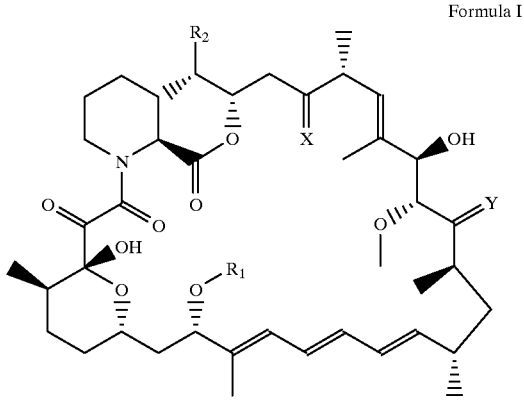

Formula I wherein $R_1$ is selected from alkyl, alkenyl, alkynyl, hydroxyalkenyl, hydroxyalkyl, hydroxyalkynyl, aryl, thioalkyl, arylalkyl, hydroxyarylalkyl, hydroxyaryl, dihydroxyalkyl, hydroxyalkoxyalkyl, hydroxyalkylarylalkyl, dihydroxyalkylarylalkyl, alkoxyalkyl, alkoxyarylalkyl, haloalkyl, haloaryl, haloarylalkyl, acyloxyalkyl, aminoalkyl, alkylaminoalkyl, alkoxycarbonylamidoalkyl, acylamidoalkyl, arylsulfonamidoalkyl, allyl, dihydroxyalkylallyl, dioxolanylallyl, carbalkoxyalkyl, and alkylsilyl; preferably an unsaturated substituent; more preferably an aromatic or alkynyl substituent; more preferably alkynyl, hydroxyalkynyl, benzyl, alkoxybenzyl, or chlorobenzyl (wherein the substituted benzyl is ortho-substituted); most preferably alkynyl or hydroxyalkynyl;

$R_2$ is selected from formula II or formula III:

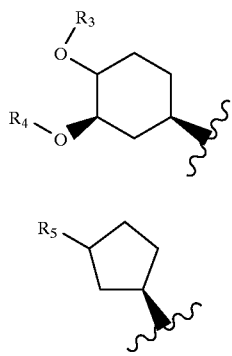

Formula II

Formula III wherein $R_3$ is selected from H, alkyl, alkenyl, alkynyl, aryl, thioalkyl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, acyloxyalkyl, aminoalkyl, alkylaminoalkyl, alkoxycarbonylamidoalkyl, acylamidoalkyl, arylsulfonamidoalkyl, allyl, dihydroxyalkylallyl, dioxolanylallyl, carbalkoxyalkyl, and alkylsilyl; preferably hydroxyalkyl, hydroxyalkoxyalkyl, acylaminoalkyl, alkoxyalkyl, and aminoalkyl; especially hydroxyethyl, hydroxypropyl, hydroxyethoxyethyl, methoxyethyl and acetylaminoethyl;

$R_4$ is H, methyl or together with $R_3$ forms $C_{2-6}$ alkylene;

$R_5$ is substituted or unsubstituted acyl (e.g., formyl, carboxy, amide or ester), oxymethyl, iminomethyl, or dioxymethylyne (e.g., —O—CH—O—); preferably (i) oxymethyl, for example, hydroxymethyl, e.g., generally $R_6O$—$CH_2$—, wherein $R_6$ is selected from H, alkyl, alkenyl, alkynyl, aryl, amino, acyl (e.g., alkylcarbonyl, arylcarbonyl, heteroarylcarbonyl, hydroxyalkylcarbonyl, aminoalkylcarbonyl, or formyl), thioalkyl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, acyloxyalkyl, aminoalkyl, alkylaminoalkyl, alkoxycarbonylamidoalkyl, acylamidoalkyl, arylsulfonamidoalkyl, allyl, dihydroxyalkylallyl, dioxolanylallyl, carbalkoxyalkyl, and alkylsilyl; (ii) acyl, for example, (4-methyl-piperazin-1-yl)-carbonyl, (morpholin-4-yl)-carbonyl, or N-methyl-N-(2-pyridin-2-yl-ethyl)-carbamoyl, e.g., generally $R_7CO$—, wherein $R_7$ is selected from H, alkyl, hydroxy, alkoxy, aryloxy, amido, alkamido, a residue of an amino acid, or N,N-disubstituted-amido wherein the substituents (a) are selected from alkyl, aryl, arylalkyl or alkylaryl or (b) form a heterocyclic structure (e.g., morpholino or piperazino); (iii) iminomethyl, for example, p-toluenesulfonylhydrazonomethyl, e.g., generally $R_8NCH$—, wherein $R_8$ is alkyl, aryl, amino, alkylamino, arylamino, or arylsulfonylamino; or (iv) dioxysubstituted dioxymethylyne compounds, e.g., O,O-(alkylene)-dioxymethylyne (i.e., wherein the two oxygens are linked by an alkylene group); and X and Y are independently selected from O, (H, OH), and (H, $OR_9$) wherein $R_9$ is selected from alkyl (preferably $C_{1-4}$ alkyl), acyl (e.g., alkylcarbonyl, arylcarbonyl, heteroarylcarbonyl, hydroxyalkylcarbonyl, aminoalkylcarbonyl, or formyl), or aryl;

wherein "alk" or "alkyl" refers to a $C_{1-10}$ (preferably $C_{1-6}$) aliphatic substituent (branched, linear, or cyclic), wherein each such "alk" or "alkyl" is optionally interrupted by an oxy (—O—) linkage; and "ar" or "aryl" refers to a monocyclic, optionally heterocyclic, optionally substituted, $C_{4-4}$ aromatic substituent (e.g., tolyl, phenyl, benzyl, pyridyl, and the like); provided that when $R_2$ is of formula II, then $R_1$ is other than methyl and (i) $R_3$ is selected from hydroxyalkyl, alkoxyalkyl, hydroxyalkoxyalkyl, acylaminoalkyl, and aminoalkyl; and/or (ii) X is other than O; and/or (iii) $R_1$ is (optionally hydroxy-substituted) alkynyl, preferably (optionally hydroxy-substituted) alk-2-ynyl, e.g. prop-2-ynyl, but-2-ynyl, pent-2-ynyl, or 4-hydroxy-but-2-ynyl; and further provided that when $R_1$ is methyl, $R_2$ is of Formula III.

Demethoxy rapamycins of Formula I also include (a) the 16-O substituted rapamycins wherein $R_1$ is selected from (i) benzyl, ortho-alkoxybenzyl, and chlorobenzyl (especially benzyl or ortho-methoxybenzyl), or (ii) (optionally hydroxy-substituted) alkynyl, preferably (optionally hydroxy-substituted) alk-2-ynyl, especially (i) prop-2-ynyl, but-2-ynyl, pent-2-ynyl, and 4hydroxy-but-2-ynyl; $R_2$ is of formula II; $R_3$ is selected from H, hydroxyalkyl, alkoxyalkyl, hydroxyalkoxyalkyl, acylaminoalkyl, and aminoalkyl; $R_4$ is methyl; and X and Y are independently selected from O, (H,OH), and (H, $C_{1-4}$alkoxy); and most preferably, the 16-O substituted rapamycins wherein $R_1$ is alkynyl or hydroxyalkynyl, especially (optionally hydroxy substituted) $C_{3-6}$ alk-2-ynyl; $R_2$ is of formula II; $R_3$ is selected from H, hydroxyalkyl, alkoxyalkyl, hydroxyalkoxyalkyl; $R_4$ is methyl; and X and Y are O;

(b) the 16-O-substituted rapamycins wherein $R_1$ is selected from alkyl, alkyenyl, alkynyl, aryl, thioalkyl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, acyloxyalkyl, aminoalkyl, alkylaminoalkyl, alkoxycarbonylamidoalkyl, acylamidoalkyl, arylsulfonamidoalkyl, allyl, dihydroxyalkylallyl, dioxolanylallyl, carbalkoxyalkyl, and alkylsilyl (especially alkynyl), wherein "alk" refers to $C_{1-10}$ aliphatic substituent (branched, linear, or cyclic), wherein each such "alk" is optionally interrupted by an oxy (—O—) linkage, and aryl refers to a monocyclic aromatic substituent; provided that where $R_1$ is methyl, the compound is 16-epi-rapamycin; $R_2$ is of formula II; $R_3$ is H; $R_4$ is methyl; and X and Y are O; and (c) the cyclopentyl rapamycins wherein $R_2$ is of Formula III, and $R_1$, $R_5$, X, and Y are as defined above; e.g., where $R_1$ is methyl, X and Y are O, and $R_5$ is substituted or unsubstituted acyl (e.g., formyl, carboxy, amide or ester), oxymethyl, iminomethyl, or dioxymethylyne (e.g., —O—CH—O—); e.g., (i) oxymethyl, e.g., $R_6O$—$CH_2$—, wherein $R_6$ is selected from H, alkyl, alkyenyl, alkynyl, aryl, thioalkyl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, acyloxyalkyl, aminoalkyl, alkylaminoalkyl, alkoxycarbonylamidoalkyl, acylamidoalkyl, arylsulfonamidoalkyl, allyl, dihydroxyalkylallyl, dioxolanylallyl, carbalkoxyalkyl, and alkylsilyl; (ii) acyl, e.g., $R_7CO$—, wherein $R_7$ is selected from H, alkyl, hydroxy, alkoxy, aryloxy, amido, alkamido, a residue of an amino acid, or N,N-substituted-amido wherein the substituent forms a heterocyclic structure (e.g., morpholino or piperazino); (iii) iminomethyl, e.g., alkyliminomethyl, aryliminomethyl, or hydrazonomethyl; or (iv) dioxysubstituted dioxymethylyne compounds, e.g., O,O-(alkylene)-dioxymethylyne (i.e., wherein the two oxygens are linked by an alkylene group); wherein "alk-" refers to a $C_{1-6}$ aliphatic group (linear, branched, or cyclic) preferably $C_{1-3}$, wherein each such "alk" may be optionally interrupted by an ether (—O—) linkage; and aryl refers to an aromatic group, preferably a monocyclic aromatic group.

Especially preferred compounds of Formula I include 1. 16-demethoxy-16-(pent-2-ynyl)oxy-rapamycin
2. 16-demethoxy-16-(but-2-ynyl)oxy-rapamycin
3. 16-demethoxy-16-(propargyl)oxy-rapamycin
4. 16-demethoxy-16-(4-hydroxy-but-2-ynyl)oxy-rapamycin
5. 16-demethoxy-16-benzyloxy-40-O-(2-hydroxyethyl)-rapamycin
6. 16-demethoxy-16-benzyloxy-rapamycin
7. 16-demethoxy-16-ortho-methoxybenzyl-rapamycin
8. 16-demethoxy-40-O-(2-methoxyethyl)-16-(pent-2-ynyl)oxy-rapamycin
9. 39-demethoxy-40-desoxy-39-formyl-42-nor-rapamycin
10. 39-demethoxy-40-desoxy-39-hydroxymethyl-42-nor-rapamycin
11. 39-demethoxy-40-desoxy-39-carboxy-42-nor-rapamycin
12. 39-demethoxy-40-desoxy-39-(4-methyl-piperazin-1-yl)carbonyl-42-nor-rapamycin
13. 39-demethoxy-40-desoxy-39-(morpholin-4-yl)carbonyl-42-nor-rapamycin
14. 39-demethoxy-40-desoxy-39-[N-methyl, N-(2-pyridin-2-yl-ethyl)]carbamoyl-42-nor-rapamycin
15. 39-demethoxy-40-desoxy-39-(p-toluenesulfonylhydrazonomethyl)-42-nor-rapamycin The compounds are produced from rapamycin or a rapamycin derivative generally as follows:

1. When the compound desired is of Formula I wherein $R_1$ is other than methyl, the modification at the 16-O can be produced either (i) by reaction of rapamycin or a rapamycin derivative with $SeO_2$ and a compound $R_1$—OH under suitable reaction conditions, e.g., at elevated temperatures, wherein $R_1$ is as defined above; or preferably (ii) by reaction of rapamycin or a rapamycin derivative with an acid, e.g., p-toluenesulphonic acid, and a nucleophile, e.g., $R_1$—OH, at room temperature, in a suitable aprotic solvent, e.g., dichloromethane, acetonitrile, or ThF.

2. When the compound desired is of formula I where $R_2$ is of formula II and $R_3$ is other than H, for example, O-alkylation at the C40 hydroxy is accomplished by reaction with an organic radical attached to a leaving group (e.g., $R_3$—Z where $R_3$ is an organic radical as defined above, e.g., an alkyl, allyl, or benzyl moiety, which is desired as the O-substituent, and Z is the leaving group, e.g., $CCl_3C(NH)O$ or $CF_3SO_3$) under suitable reaction conditions, e.g., in the presence of an acid like trifluoromethanesulfonic acid, camphorsulfonic acid, p-toluenesulfonic acid or their respective pyridinium or substituted pyridinium salts when Z is $CCl_3C(NH)O$ or in the presence of a base like pyridine, a substituted pyridine, diisopropylethylamine or pentamethylpiperidine when Z is $CF_3SO_3$, or analogously to the methods described in U.S. Pat. No. 5,258,389 or PCT/EP 93/02604 for 40-O alkylation of rapamycin.

3. When the compound desired is of formula I where $R_2$ is of formula III, conversion of the cyclohexyl ring of formula II to the cyclopentyl ring of formula III is accomplished by reaction with morpholinosulphur trifloride to obtain the aldehyde compound (e.g., where $R_5$ is formyl). This compound thus obtained may then be oxidized from the aldehyde to the carboxylic acid (e.g., where $R_5$ is carboxy), or reduced from the aldehyde to the alcohol (e.g., where $R_5$ is hydroxymethyl). Further O-substitution or modification to make the other compounds of the invention is performed according to processes known to those skilled in the art, e.g., the following general processes: (i) for oxymethyl derivatives, the alcohol compound is reacted analogously as described above for 40-O-substitution; (ii) for acyl derivatives, the carboxylic acid compound is reacted with the desired amine or alcohol in the presence of an activating or coupling reagent, e.g., oxalylchloride or dicyclohexylcarbodiimide, to give the desired amide or ester compounds respectively; and (iii) for iminomethyl or dioxymethylyne compounds, the aldehyde compound is condensed with the desired amine or alkylenediol, respectively, under acidic conditions.

4. When the compound desired is of formula I where X is other than O, the 32-O dihydro compound (where X is (H,OH) ) is prepared by O-protecting the hydroxy groups, e.g., at positions 28 and 40 of rapamycin, e.g., using triethylsilyl ether protecting groups, reducing the protected compound, e.g., using L-selectride, and optionally deprotecting, e.g., under mildly acidic conditions, analogously to the method described in U.S. Pat. No. 5,256,790 for preparation of 32-O-dihydro-rapamycin from rapamycin. Where substitution at the 32 hydroxy is desired, the 28,40-O,O-protected compound is alkylated, e.g., as described for 40-O alkylation above, acylated, or otherwise O-substituted, e.g., analogously to the procedures described in U.S. Pat. No. 5,256,790.

The above processes may be carried out in any order, preferably using rapamycin as the ultimate starting material. Where necessary, the starting materials and intermediates may be protected (e.g., O-protected as described in process 4) before carrying out the above reaction(s) and then deprotected to obtain the desired final product.

The Novel Compounds are particularly useful for the following conditions:

a) Treatment and prevention of organ or tissue transplant rejection, e.g. for the treatment of recipients of e.g. heart, lung, combined heart-lung, liver, kidney, pancreatic, skin or corneal transplants; including treatment and prevention of acute rejection; treatment and prevention of hyperacute rejection, e.g., as associated with xenograft rejection; and treatment and prevention of chronic rejection, e.g., as associated with graft-vessel disease. The Novel Compounds are also indicated for the treatment and prevention of graft-versus-host disease, such as following bone marrow transplantation.

b) Treatment and prevention of autoimmune disease and of inflammatory conditions, in particular inflammatory conditions with an etiology including an autoimmune component such as arthritis (for example rheumatoid arthritis, arthritis chronica progrediente and arthritis deformans) and rheumatic diseases. Specific auto-immune diseases for which the compounds of the invention may be employed include, autoimmune hematological disorders (including e.g. hemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine ophthalmopathy, Graves disease, sarcoidosis, multiple sclerosis, primary billiary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephrotic syndrome or minimal change nephropathy) and juvenile dermatomyositis.

c) Treatment and prevention of asthma.

d) Treatment of multi-drug resistance (MDR). The Novel Compounds suppress P-glycoproteins (Pgp), which are the membrane transport molecules associated with MDR. MDR is particularly problematic in cancer patients and AIDS patients who will not respond to conventional chemotherapy because the medication is pumped out of the cells by Pgp. The Novel Compounds are therefore useful for enhancing the efficacy of other chemotherapeutic agents in the treatment and control of multidrug resistant conditions such as multidrug resistant cancer or multidrug resistant AIDS.

e) Treatment of proliferative disorders, e.g. tumors, hyperproliferative skin disorder and the like.

f) Treatment of fungal infections.

g) Treatment and prevention of inflammation, especially in potentiating the action of steroids.

h) Treatment and prevention of infection, especially infection by pathogens having Mip or Mip-like factors.

The invention thus provides the Novel Compounds described herein, for use as novel intermediates or as pharmaceuticals, methods of treating or preventing the above-described disorders by administering an effective amount of a Novel Compound to a patient in need thereof, use of a Novel Compound in the manufacture of a medicament for treatment or prevention of the above-described disorders, and pharmaceutical compositions comprising a Novel Compound in combination or association with a pharmaceutically acceptable diluent or carrier.

The Novel Compounds are utilized by administration of a pharmaceutically effective dose in pharmaceutically acceptable form to a subject in need of treatment. Appropriate dosages of the Novel Compounds will of course vary, e.g. depending on the condition to be treated (for example the disease type or the nature of resistance), the effect desired and the mode of administration.

In general however satisfactory results are obtained on administration orally at dosages on the order of from 0.05 to 5 or up to 10 mg/kg/day, e.g. on the order of from 0.1 to 2 or up to 7.5 mg/kg/day administered once or, in divided doses 2 to 4× per day, or on administration parenterally, e.g. intravenously, for example by i.v. drip or infusion, at dosages on the order of from 0.01 to 2.5 up to 5 mg/kg/day, e.g. on the order of from 0.05 or 0.1 up to 1.0 mg/kg/day. Suitable daily dosages for patients are thus on the order of 500 mg p.o., e.g. on the order of from 5 to 100 mg p.o., or on the order of from 0.5 to 125 up to 250 mg i.v., e.g. on the order of from 2.5 to 50 mg i.v.

Alternatively and even preferably, dosaging is arranged in patient specific manner to provide predetermined trough blood levels, e.g. as determined by RIA technique. Thus patient dosaging may be adjusted so as to achieve regular on-going trough blood levels as measured by RIA on the order of from 50 or 150 up to 500 or 1000 ng/ml, i.e. analogously to methods of dosaging currently employed for Ciclosporin immunosuppressive therapy.

The Novel Compounds may be administered as the sole active ingredient or together with other drugs. For example, in immunosuppressive applications such as prevention and treatment of graft vs. host disease, transplant rejection, or autoimmune disease, the Novel Compounds may be used in combination with cyclosporins or ascomycins, or their immunosuppressive analogs, e.g., cyclosporin A, cyclosporin G, FK-506, etc.; corticosteroids; cyclophosphamide; azathioprene; methotrexate; brequinar, leflunomide; mizoribine; immunosuppressive monoclonal antibodies, e.g., monoclonal antibodies to leukocyte receptors, e.g., MHC, CD2, CD3, CD4, CD7, CD25, CD28, CTLA4, B7, CD45, or CD58 or their ligands; or other immunomodulatory compounds.

For immunosuppressive applications, e.g., treatment and prevention of organ or tissue transplant rejection, the combination is most preferably with IL-2 transcription inhibitors such as the immunosuppressive cyclosprins (e.g., cyclosporin A) and ascomycins (e.g., FK-506). For anti-inflammatory applications, the Novel Compounds can also be used together with anti-inflammatory agents, e.g., corticosteroids. For anti-infective applications, the Novel Compounds can be used in combination with other anti-infective agents, e.g., anti-viral drugs or antibiotics.

The Novel Compounds are administered by any conventional route, in particular enterally, e.g. orally, for example in the form of solutions for drinking, tablets or capsules or parenterally, for example in the form of injectable solutions or suspensions. Suitable unit dosage forms for oral administration comprise, e.g. from 1 to 50 mg of a compound of the invention, usually 1 to 10 mg. Pharmaceutical compositions comprising the novel compounds may be prepared analogously to pharmaceutical compositions comprising rapamycin, e.g., as described in EPA 0 041 795, which would be evident to one skilled in the art.

The pharmacological activities of the Novel Compounds are demonstrated in, e.g., the following tests:

1. Mixed lymphocyte reaction (MLR)

The Mixed Lymphocyte Reaction was originally developed in connection with allografts, to assess the tissue compatibility between potential organ donors and recipients, and is one of the best established models of immune reaction in vitro. A murine model MLR, e.g., as described by T. Meo in "Immunological Methods", L. Lefkovits and B. Peris, Eds., Academic Press, N.Y. pp. 227–239 (1979), is used to demonstrate the immunosuppressive effect of the Novel Compounds. Spleen cells ($0.5 \times 10^6$) from Balb/c mice (female, 8–10 weeks) are co-incubated for 5 days with $0.5 \times 10^6$ irradiated (2000 rads) or mitomycin C treated spleen cells from CBA mice (female, 8–10 weeks). The irradiated allogeneic cells induce a proliferative response in the Balb/c spleen cells which can be measured by labeled precursor incorporation into the DNA.

Since the stimulator cells are irradiated (or mitomycin C treated) they do not respond to the Balb/c cells with proliferation but do retain their antigenicity. The antiproliferative effect of the Novel Compounds on the Balb/c cells is measured at various dilutions and the concentration resulting in 50% inhibition of cell proliferation ($IC_{50}$) is calculated. All of the exemplified Novel Compounds are active in this assay. The alkynyl derivatives of the examples are particularly potent immunosuppressants, with an $IC_{50}$ in this assay relative to rapamycin of 0.3–0.8, i.e., up to 3× more active than rapamycin.

2. IL-6 mediated proliferation

The capacity of the Novel Compounds to interfere with growth factor associated signalling pathways is assessed using an interleukin-6 (IL-6)-dependent mouse hybridoma cell line. The assay is performed in 96-well microtiter plates. 5000 cells/well are cultivated in serum-free medium (as described by M. H. Schreier and R. Tees in Immunological Methods, I. Lefkovits and B. Pemis, eds., Academic Press 1981, Vol. II, pp. 263–275), supplemented with I ng recombinant IL-6/ml. Following a 66 hour incubation in the absence or presence of a test sample, cells are pulsed with 1 µCi (3-H)-thymidine/well for another 6 hours, harvested and counted by liquid scintillation. (3-H)-thymidine incorporation into DNA correlates with the increase in cell number and is thus a measure of cell proliferation. A dilution series of the test sample allows the calculation of the concentration resulting in 50% inhibition of cell proliferation ($IC_{50}$). All of the exemplified Novel Compounds are active in this assay. The alkynyl derivatives of the examples are particularly potent immunosuppressants, with an $IC_{50}$ in this assay relative to rapamycin of from 0.2 to 0.9, i.e., up to 5× more active than rapamycin.

3. Macrophilin binding assay

Rapamycin and the structurally related immunosuppressant, FK-506, are both known to bind in vivo to macrophilin-12 (also known as FK-506 binding protein or FKBP-12), and this binding is thought to be related to the immunosuppressive activity of these compounds. The Novel Compounds also bind strongly to macrophilin-12, as is demonstrated in a competitive binding assay. In this assay, FK-506 coupled to BSA is used to coat microtiter wells. Biotinylated recombinant human macrophilin-12 (biot-MAP) is allowed to bind in the presence or absence of a test sample to the immobilized FK-506. After washing (to remove non-specifically bound macrophilin), bound biot-MAP is assessed by incubation with a streptavidin-alkaline phosphatase conjugate, followed by washing and subsequent addition of p-nitrophenyl phosphate as a substrate. The read-out is the OD at 405 nm. Binding of a test sample to biot-MAP results in a decrease in the amount of biot-MAP bound to the FK-506 and thus in a decrease in the OD405. A dilution series of the test sample allows determination of the concentration resulting in 50% inhibition of the biot-MAP binding to the immobilized FK-506 ($IC_{50}$). The exemplified Novel Compounds all exhibit good binding to FKBP in this assay.

4. Localized Graft-Versus-Host (GvH) Reaction

In vivo efficacy of the Novel Compounds is proved in a suitable animal model, as described, e.g., in Ford et al, TRANSPLANTATION 10 (1970) 258. Spleen cells ($1 \times 10^7$) from 6 week old female Wistar/Furth (WF) rats are injected subcutaneously on day 0 into the left hind-paw of female (F344×WF)$F_1$ rats weighing about 100 g. Animals are treated for 4 consecutive days and the popliteal lymph nodes are removed and weighed on day 7. The difference in weight between the two lymph nodes is taken as the parameter for evaluating the reaction.

5. Kidney Allograft Reaction in Rat

One kidney from a female fisher 344 rat is transplanted onto the renal vessel of a unilaterally (left side) nephrectomized WF recipient rat using an end-to-end anastomosis. Ureteric anastomosis is also end-to-end. Treatment commences on the day of transplantation and is continued for 14 days. A contralateral nephrectomy is done seven days after transplantation, leaving the recipient relying on the performance of the donor kidney. Survival of the graft recipient is taken as the parameter for a functional graft.

6. Experimentally Induced Allergic Encephalomyelitis (EAE) in Rats

Efficacy of the Novel Compounds in EAE is measured, e.g., by the procedure described in Levine & Wenk, AMER J PATH 47 (1965) 61; McFarlin et al, J IMMUNOL 113 (1974) 712; Borel, TRANSPLANT. & CLIN. IMMUNOL 13 (1981) 3. EAE is a widely accepted model for multiple sclerosis. Male Wistar rats are injected in the hind paws with a mixture of bovine spinal cord and complete Freund's adjuvant. Symptoms of the disease (paralysis of the tail and both hind legs) usually develop within 16 days. The number of diseased animals as well as the time of onset of the disease are recorded.

7. Freund's Adjuvant Arthritis

Efficacy against experimentally induced arthritis is shown using the procedure described, e.g., in Winter & Nuss, ARTHRITIS & RHEUMATISM 9 (1966) 394; Billingham & Davies, HANDBOOK OF EXPERIMENTAL PHARMACOL (Vane & Ferreira Eds, Springer-Verlag, Berlin) 50/II (1979) 108–144. OFA and Wistar rats (male or female, 150 g body weight) are injected i.c. at the base of the tail or in the hind paw with 0.1 ml of mineral oil containing 0.6 mg of lyophilized heat-killed *Mycobacterium smegmatis*. In the developing arthritis model, treatment is started immediately after the injection of the adjuvant (days 1–18); in the established arthritis model treatment is started on day 14, when the secondary inflammation is well developed (days 14–20). At the end of the experiment, the swelling of the joints is measured by means of a micro-caliper. $ED_{50}$ is the oral dose in mg/kg which reduces the swelling (primary or secondary) to half of that of the controls.

8. Antitumor and MDR activity

The antitumor activity of the Novel Compounds and their ability to enhance the performance of antitumor agents by alleviating multidrug resistance is demonstrated, e.g., by administration of an anticancer agent, e.g., colchicine or etoposide, to multidrug resistant cells and drug sensitive cells in vitro or to animals having multidrug resistant or drug sensitive tumors or infections, with and without co-administration of the Novel Compounds to be tested, and by administration of the Novel Compound alone. Such in vitro testing is performed employing any appropriate drug resistant cell line and control (parental) cell line, generated, e.g. as described by Ling et al., J. Cell. Physiol. 83, 103–116 (1974) and Bech-Hansen et al. J. Cell. Physiol. 88, 23–32 (1976). Particular clones chosen are the multi-drug resistant (e.g. coichicine resistant) line CHR (subclone C5S3.2) and the parental, sensitive line AUX B1 (subclone AB1 S11). In vivo anti-tumor and anti-MDR activity is shown, e.g., in mice injected with multidrug resistant and drug sensitive cancer cells. Ehrlich ascites carcinoma (EA) sub-lines resistant to drug substance DR, VC, AM, ET, TE or CC are developed by sequential transfer of EA cells to subsequent generations of BALB/c host mice in accordance with the methods described by Slater et al., J. Clin. Invest, 70, 1131 (1982). Equivalent results may be obtained employing the Novel Compounds test models of comparable design, e.g. in vitro, or employing test animals infected with drug-resistant and drug sensitive viral strains, antibiotic (e.g. penicillin) resistant and sensitive bacterial strains, anti-mycotic resistant and sensitive fungal strains as well as drug resistant protozoal strains, e.g. Plasmodial strains, for example naturally occurring sub-strains of *Plasmodium falciparum* exhibiting acquired chemotherapeutic, anti-malarial drug resistance.

9. Steroid potentiation

The macrophilin binding activity of the Novel Compounds also makes them useful in enhancing or potentiating the action of corticosteroids. Combined treatment with the compounds of the invention and a corticosteroid, such as dexamethasone, results in greatly enhanced steroidal activity. This can be shown, e.g., in the murine mammary tumor virus-chloramphenicol acetyltransferase (MMTV-CAT)

reporter gene assay, e.g., as described in Ning, et al., *J. Biol. Chem.* (1993) 268: 6073. This synergistic effect allows reduced doses of corticosteroids, thereby reducing the risk of side effects in some cases.

10. Mip and Mip-like factor inhibition

Additionally, the Novel Compounds bind to and block a variety of Mip (macrophage infectivity potentiator) and Mip-like factors, which are structurally similar to macrophilin. Mip and Mip-like factors are virulence factors produced by a wide variety of pathogens, including those of the genera Chlamidia, e.g., *Chlamidia trachomatis;* Neisseria, e.g., *Neisseria meningitidis;* and Legionella, e.g., *Legionella pneumophilia*; and also by the obligately parasitic members of the order Rickettsiales. These factors play a critical role in the establishment of intracellular infection. The efficacy of the Novel Compounds in reducing the infectivity of pathogens which produce Mip or Mip-like factors can be shown by comparing infectivity of the pathogens in cells culture in the presence and absence of the macrolides, e.g., using the methods described in Lundemose, et al., *Mol. Microbiol.* (1993) 7: 777.

The Novel Compounds are also useful in assays to detect the presence or amount of macrophilin-binding compounds, e.g., in competitive assays for diagnostic or screening purposes. Thus, in another embodiment, the invention provides for use of the Novel Compounds as a screening tool to determine the presence of macrophilin-binding compounds in a test solution, e.g., blood, blood serum, or test broth to be screened. Preferably, a Novel Compound is immobilized in microtiter wells and then allowed to bind in the presence and absence of a test solution to labelled macrophilin-12 (FKBP-12). Alternatively, the FKBP-12 immobilized in microtiter wells and allowed to bind in the presence and absence of a test solution to a Novel Compound which has been labelled, e.g., fluoro-, enzymatically- or radio-labelled, e.g., a Novel Compound of Formula I wherein R, comprises a labelling group. The plates are washed and the amount of bound labelled compound is measured. The amount of macrophilin-binding substance in the test solution is roughly inversely proportional to the amount of bound labelled compound. For quantitative analysis, a standard binding curve is made using known concentrations of macrophilin binding compound.

The following examples are intended to illustrate rather than limit the invention. Characteristic spectrascopic data is provided to aid in identification of the compounds.

EXAMPLE 1

16-demethoxy-16-(pent-2-ynyl)oxy-rapamycin

To a solution of 0.6 ml 2-pentyn-1-ol in 5 ml $CH_2Cl_2$ are added 456 mg rapamycin followed by 5 mg p-toluenesulfonic acid. The mixture is stirred for 2 h at room temperature. Then the reaction is quenched with 7 ml of a saturated aqueous solution of $NaHCO_3$. The aqueous phase is separated and extracted 2× with 10 ml ethyl acetate. The organic phases are combined, dried over sodium sulfate and the solvent evaporated. The residue is chromatographed over silica gel, eluting with ethyl acetate/hexane 3/2. The crude product is finally purified by preparative HPLC (RP-18, 250×10 mm, MeOH/H2O 80/20, 3 ml/min).

MS (FAB) m/z 972 (M+Li)

H-NMR (CDCl3)(major isomer) d: 0.67 (1H, q); 1.13 (3H, t); 1.67 (3H,s); 1.74 (3H, s); 3.33 (3H, s); 3.40 (3H, s); 3.73 (1H, d); 3.77 (1H, dm); 4.01 (1H, dm); 4.16 (1H, d); 4.66 (1H, s).

EXAMPLE 2

16-demethoxy-16-(but-2-ynyl)oxy-rapamycin

To a solution of 0.4 ml 2-butyn-1-ol in 3 ml $CH_2Cl_2$ are added 251 mg rapamycin followed by 4 mg p-toluenesulfonic acid. The mixture is stirred for 2 h at room temperature. Then the reaction is quenched with 7 ml of a saturated aqueous solution of NaHCO3. The aqueous phase is separated and extracted 2× with 10 ml ethyl acetate. The organic phases are combined, dried over sodium sulfate and the solvent evaporated. The residue is chromatographed over silica gel, eluting with ethyl acetate/hexane 3/2. The crude product is finally purified by preparative HPLC (RP-18, 250×10 mm, MeOH/H2O 80/20, 3 ml/min).

MS (FAB) m/z 958 (M+Li)

H-NMR (CDCl3)(major isomer) d: 0.67 (1H, q); 1.67 (3H,s); 1.74 (3H, s); 1.83 (1H, bs); 3.33 (3H, s); 3.40 (3H, s); 3.72 (1H, d); 3.75 (1H, dm); 4.01 (1H, dm); 4.16 (1H, d); 4.73 (1H, s).

EXAMPLE 3

16-demethoxy-16-(proparyl)oxy-rapamycin

To a solution of 0.3 ml propargyl alcohol in 3 ml $CH_2Cl_2$ are added 251 mg rapamycin followed by 4 mg p-toluenesulfonic acid. The mixture is stirred for 2 h at room temperature. Then the reaction is quenched with 7 ml of a saturated aqueous solution of NaHCO3. The aqueous phase is separated and extracted 2× with 10 ml ethyl acetate. The organic phases are combined, dried over sodium sulfate and the solvent evaporated. The residue is chromatographed over silica gel, eluting with ethyl acetate/hexane 3/2. The crude product is finally purified by preparative HPLC (RP-18, 250×10 mm, MeOH/H2O 80/20, 3 ml/min).

MS (FAB) m/z 944 (M+Li)

H-NMR (CDCl3)(major isomer) d: 0.68 (1H, q); 1.66 (3H,s); 1.74 (3H, s); 2.32 (1H, bt); 3.34 (3H, s); 3.41 (3H, s); 3.67 (1H, d); 3.83 (1H, dm); 4.08 (1H, dm); 4.16 (1H, d); 4.84 (1H, s).

EXAMPLE 4

16-demethoxy-16-(4-hydroxy-but-2-ynyl)oxy-rapamycin

To a suspension of 940 mg 2-butyn-1,4-diol in 6 ml $CH_2Cl_2$ are added 502 mg rapamycin followed by 5 mg p-toluenesulfonic acid. The mixture is stirred for 2 h at room temperature. Then the reaction is quenched with 10 ml of a saturated aqueous solution of $NaHCO_3$. The aqueous phase is separated and extracted 2× with 10 ml ethyl acetate. The organic phases are combined, dried over sodium sulfate and the solvent evaporated. The residue is chromatographed over silica gel, eluting with ethyl acetate/hexane 4/1. The crude product is finally purified by preparative HPLC (RP-18, 250×25 mm, MeOH/H2O 75/25, 7 ml/min).

MS (FAB) m/z 974 (M+Li)

H-NMR (CDCl3)(major isomer) d: 0.67 (1H, q); 1.67 (3H,s); 1.75 (3H, s); 3.33 (3H, s); 3.41 (3H, s); 3.73 (1H, d); 3.81 (1H, dm); 4.08 (1H, dm); 4.17 (1H, d); 4.28 (2H, bs); 4.67 (1H, s).

EXAMPLE 5

16-demethoxy-16-benzyloxy-40-O-(2-hydroxyethyl)-rapamycin

To a solution of 0.6 ml benzyl alcohol in 3 ml $CH_2Cl_2$ are added 264 mg 40-O-(2-hydroxyethyl)-rapamycin (prepared as described in WO 94/09010) followed by 5 mg p-toluenesulfonic acid. The mixture is stirred for 1 h at room temperature. Then the reaction is quenched with 7 ml of a saturated aqueous solution of NaHCO₃. The aqueous phase is separated and extracted 2× with 10 ml diethyl ether. The organic phases are combined, dried over sodium sulfate and the solvent evaporated. The residue is chromatographed over silica gel, eluting with ethyl hexane/acetone 4/1 followed by hexane/acetone 1/1. The crude product is finally purified by preparative HPLC (RP-18, 250×25 mm, CH3CN/H2O 75/25, 8 ml/min).

MS (FAB) m/z 1040 (M+Li)

H-NMR (CDCl3)(major isomer) d: 0.72 (1H, q); 1.73 (6H, bs); 3.32 (3H, s); 3.43 (3H, s); 3.7 (4H, m); 4.15 (1H, d); 4.18 (1H, d); 4.47 (1H, d)); 4.80 (1H, s); 7.3 (5H, m).

EXAMPLE 6

6-demethoxy-16-benzyloxy-rapamycin 1 mmol rapamycin is dissolved in 50 ml methylene chloride containing 3 ml of benzyl alcohol. 0.1 mmol of p-toluenesulphonic acid is added, and the reaction mixture is then stirred at room temperature for 2–10 hours. The reaction mixture is then poured in a saturated solution of sodium bicarbonate. The organic layer is separated, dried over sodium sulphate, and the solvent evaporated. The crude product is then purified by HPLC to give the pure title compound as a white powder.

EXAMPLE 7

16-demethoxy-16-(ortho-methoxybenzyl)oxy-rapamycin

To a solution of 0.76 g of ortho-methoxy-benzyl alcohol in 3 ML CH₂Cl₂ are added 250 mg of rapamycin followed by 5 mg of p-toluenesulfonic acid. The mixture is stirred for 8 h at room temperature and the reaction is quenched with 5 mL of a saturated aqueous solution of NaHCO₃. The layers are separated and the aqueous layer is extracted 2× with 10 mL ether. The combined organic solution is dried over sodium sulfate, filtered and concentrated under reduced pressure. The residue is chromatographed over silica gel, using hexane/acetone (4/1 to 3/2) as the eluent. The resulting product is further purified by preparative HPLC (RP-18, 250×25 mm, CH₃CN/H₂O 75/25, 8 mL/min).

MS (FAB) m/z 1026 (M+Li)

H-NMR (CDCl) (major isomer) δ: 0.67 (1H, q); 1.73 and 1.74 (6H, 2s); 3.33 (3H, s); 3.41 (3H, s); 3.72 (1H, d); 3.81 (3H, s); 4.18 (1H, broad d); 4.26 (1H, d); 4.45 (1H, d); 4.72 (1H, broad s); 6.83 (1H, d); 6.92 (1H, m); 7.23 (1H, m); 7.32 (1H, m).

EXAMPLE 8

16-demethoxy-40-O-(2-methoxyethyl)-16-(pent-2-ynyl)oxy-rapamycin

To a solution of 0.7 ml 2-pentyn-1-ol in 5 ml CH₂Cl₂ are added 486 mg of 40-O-(2-methoxyethyl)-rapamycin followed by 5 mg p-toluenesulfonic acid. The mixture is stirred for 2 h at room temperature. Then the reaction is quenched with 7 ml of a saturated aqueous solution of NaHCO₃. The aqueous phase is separated and extracted 2× with 10 ml ethyl acetate. The organic phases are combined, dried over sodium sulfate and the solvent evaporated. The residue is chromatographed over silica gel, eluting with ethyl acetate/hexane 1/1. The crude product is finally purified by preparative HPLC (RP-18, 250×25 mm, MeOH/H2O 83/17, 7 ml/min).

MS (FAB) m/z 1030 (M+Li)

H-NMR (CDCl3)(major isomer) d: 0.72 (1H, q); 1.14 (3H, t); 1.67 (3H,s); 1.74 (3H, s); 3.33 (3H, s); 3.38 (3H, s); 3.45 (3H, s); 3.73 (1H, d); 3.77 (1H, dm); 4.01 (1H, dm); 4.17 (1H, d); 4.65 (1H, s).

EXAMPLE 9

39-demethoxy-40-desoxy-39-formyl-42-nor-rapamycin

To a solution of 1.85 g of rapamycin in 40 ml acetonitrile at −30 C. are added 365 μl morpholinosulphur trifluoride. The reaction mixture is kept 1 h at −30 C., 1 h at 0 C. and then quenched with a saturated aqueous bicarbonate solution. The aqueous phase is extracted 3× with 30 ml ethyl acetate, and the organic phases are combined and dried over sodium sulfate. After evaporation of the solvent, the crude product is purified by column chromatography over silica gel, eluting with hexane/acetone 4/1.

MS (FAB, LiI matrix): 888 (M+Li)

H-NMR (CDCl3): 3.13 (s, 3H); 3.34 (s, 3H); 9.62 (d, 1H); no other singulet between 3.0 and 3.6 ppm. No signal between 0.6 and 0.85 ppm.

EXAMPLE 10

39-demethoxy-40-desoxy-39-hydroxymethyl-42-nor-rapamycin

A solution of 44 mg 39-demethoxy-4O-desoxy-39-formyl-42-nor-rapamycin in 1.2 ml of THF/water 5/1 is treated with 1.5 mg of t-butylamine/borane complex for 2 h at 0 C. the reaction mixture is then poured on 2 ml HCl 0.1N and extracted with 3×5 ml ethyl acetate. The organic phases are combined, washed with 2 ml of a saturated sodium bicarbonate solution and dried over sodium sulfate. The solvent is evaporated in vacuo, and the crude product is purified by column chromatography over silica gel eluting with hexane/ethyl acetate 1/1.

MS (FAB, LiI matrix): 890 (M+Li)

H-NMR (CDCl3): 3.13 (s, 3H); 3.33 (s, 3H); 4.18 (m, 2H). No signal between 0.5 and 0.85 ppm., no aldehyde proton at 9.62 ppm.

EXAMPLE 11

39-demethoxy-40-desoxy-39-carboxy-42-nor-rapamycin

A solution of 85 mg NaOCl and 113 mg NaH₂PO₄ in 2 ml water is added to a solution of 111 mg 39-demethoxy-40-desoxy-39-formyl-42-nor-rapamycin and 0.2 ml 2-methyl-2-butene in 4 ml t-butanol. The mixture is stirred at room temperature for 2 h. The solvents are then evaporated and the residue extracted with 3×5 ml ethyl acetate. The organic phases are combined, dried over anhydrous sodium sulfate and the solvent evaporated. The product is purified by preparative HPLC (RP-18, 250×10 mm, acetonitrile/water 60/40, 3 ml/mn).

MS (FAB, LiI matrix): 904 (M+Li)

H-NMR(CDCl3): 1.65 (s, 3H); 1.78 (s, 3H); 3.13(s, 3H); 3.33(s, 3H); 3.75 (d, 1H); 4.18 (d, 1H). No signal below 0.85 ppm. No additional singulet in the region 3.0–3.6 ppm.

EXAMPLE 12

39-demethoxy -40-desoxy-39-(4-methyl-piperazin-1-yl)carbonyl-42-nor-rapamycin To a stirred solution of 180 mg 39-carboxy-39-demethoxy-40-desoxy-42-nor-rapamycin in 4 ml THF at −75 C. are added 0.08 ml pyridine followed by 0.04 ml oxalyl chloride. The reaction mixture is kept at −75 C. for 30 minutes after which 0.09 ml N-methyl-piperazine are added. The reaction is stirred for an additional hour and then quenched with 5 ml of saturated aqueous sodium bicarbonate and 5 ml ethyl acetate. The water phase is separated and extracted with 2×5 ml ethyl acetate. The organic phases are combined, dried over sodium sulfate and the solvent evaporated. The crude product is purified by preparative HPLC (RP-18, 250×10 mm, MeOH/H2O 85/15, 3 ml/mn).

MS (FAB) m/z 986 (M+Li)

H-NMR (CDCl3) d=1.65 (3H, s); 1.78 (3H, s); 2.31 (3H, s); 2.4 (4H, m); 3.13 (3H, s); 3.34 (3H, s); 3.79 (1H, d); 4.21 (1H, d); 4.68 (1H, bs).

EXAMPLE 13

39-demethoxy-40-desoxy-39-(morpholin-4yl)carbonyl-42-nor-rapamycin

This compound is obtained following the method of Example 11, using morpholine instead of N-methyl-piperazine.

MS (FAB) m/z 973 (M+Li)

H-NMR (CDCl3) d=1.65 (3H, s); 1.77 (3H, s); 3.13 (3H, s); 3.33 (3H, s); 3.6 (4H, m); 3.77 (1H, d); 4.19 (1H, d); 4.66 (1H, bs).

EXAMPLE 14

39-demethoxy-40-desoxy-39-[N-methyl, N-(2-pyridin-2-yl-ethyl)]carbamoyl-42-nor-rapamycin This compound is obtained following the method of Example 11 using (2-pyridin-2-yl-ethyl)methylamine instead of N-methyl-piperazine.

MS (FAB) m/z 1022 (M+Li)

H-NMR (CDCl3) d=1.66 (3H, s); 1.78 (3H, s); 2.93 (3H, s); 3.13 (3H, s); 3.33 (3H, s); 4.23 (1H, m); 4.67 (1H, s); 7.1 (2H, m); 7.6 (1H, m); 8.51 (1H, d).

EXAMPLE 15

39-demethoxy-40-desoxy-39-(p-toluenesulfonylhydrazonomethyl)-42-nor-rapamycin To a mixture of 523 mg 39-demethoxy-40-desoxy-39-formyl-42-nor-rapamycin in 10 ml acetonitrile are added 156 mg p-toluenesulfonylhydrazide. The reaction mixture is stirred for 30 minutes at room temperature and then the solvent is evaporated. The residue is chromatographed over silica gel, eluting with hexane/acetone 5/1, to give the title compound.

MS (FAB) m/z 1056 (M+Li)

H-NMR (CDCl3) d=1.65 (3H, s); 1.76 (3H, s); 2.43 (3H, s); 3.13 (3H, s); 3.34 (3H, s); 3.79 (1H, d); 4.18 (1H, d); 4.69 (1H, bs); 7.13 (1H, d); 7.32 (2H, d); 7.56 (1H, s); 7.80 (2H, d).

We claim:
1. A compound of Formula I:

wherein
$R_1$ is:
  optionally hydroxy-substituted alkynyl;
$R_2$ is of Formula II or Formula III:

$R_3$ is:
  H, alkyl, alkyenyl, (optionally hydroxy-substituted) alkynyl, aryl, thioalkyl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, aminoalkyl, alkylaminoalkyl, alkoxycarbonylamidoalkyl, arylsulfonamidoalkyl, allyl, dihydroxyalkylallyl, dioxolanylallyl, carbalkoxyalkyl, or alkylsilyl;
$R_4$ is H or methyl, or $R_4$ together with $R_3$ forms $C_{2-6}$ alkylene;
$R_5$ is:
  $R_6O$—$CH_2$— wherein $R_6$ is H, alkyl, alkenyl, alkynyl, aryl, amino, alkylcarbonyl, arylcarbonyl, heteroarylcarbonyl, hydroxyalkylcarbonyl, aminoalkylcarbinyl, formyl, thioalkyl, arylalkyl, hydroxyarylalkyl, hydroxyaryl, hydroxyalkyl, dihydroxyalkyl, hydroxyalkoxyalkyl, hydroxyalkylarylalkyl, dihydroxyalkylarylalkyl, alkoxyalkyl, aminoalkyl, alkylaminoalkyl, alkoxycarbonylamidoalkyl, arylsulfonamidoalkyl, allyl, dihydroxyalkylallyl, dioxolanylallyl, carbalkoxyalkyl or alkylsilyl,
  $R_7CO$— where $R_7$ is H, alkyl, hydroxy, alkoxy, aryloxy, amido, alkamido, a residue of an amino acid, or N,N-disubstituted-amido wherein each substituent of N is independently alkyl, aryl, arylakyl or alkylaryl, or both such substituents together form morpholino or piperazino, $R_8NCH$— where $R_8$ is alkyl, aryl, amino, alkylamino, arylamino, or arylsulfonylamino, or O,O-(alkylyne) dioxymethylyne;

each X and Y is independently O, (H, OH), or (H, OR$_9$); and R$_9$ is:

alkyl, alkylcarbonyl, arylcarbonyl, heteroarylcarbonyl, hydroxyalkylcarbonyl, aminoalkylcarbonyl, formyl or aryl;

"alk" or "alkyl" refer to a $C_{1-10}$ aliphatic substituent, each such "alk" or "alkyl" being optionally interrupted by an oxy (—O—) linkage; and "ar" or "aryl" refer to substituted or unsubstituted tolyl, phenyl, benzyl, or pyridyl.

2. A compound according to claim 1 wherein $R_1$ is (optionally hydroxy-substituted) alkynyl; $R_2$ is of formula II; $R_3$ is selected from H, hydroxyalkyl, alkoxyalkyl, hydroxyalkoxyalkyl, and aminoalkyl; $R_4$ is methyl; and X and Y are independently selected from O, (H, OH) and (H, $C_{1-4}$ alkoxy).

3. A compound according to claim 2 wherein $R_1$ is alkynyl.

4. A compound according to claim 2 wherein $R_1$ is (optionally hydroxy-substituted) $C_{3-6}$alk-2-ynyl.

5. A compound according to claim 2 wherein $R_1$ is (optionally hydroxy-substituted) $C_{3-6}$ alk-2-ynyl; $R_2$ is of Formula II; $R_3$ is selected from H, hydroxyalkyl, alkoxyalkyl and hydroxyalkoxyalkyl; $R_4$ is methyl; and X and Y are O.

6. A compound according to claim 1 wherein $R_2$ is of Formula III.

7. A compound according to claim 1 wherein $R_1$ is alkynyl.

8. A compound according to claim 1 wherein $R_1$ is (optionally hydroxy-substituted) $C_{3-6}$alk-2-ynyl.

9. A compound according to claim 1 wherein $R_1$ is prop-2-ynyl, but-2-ynyl, pent-2-ynyl or 4-hydroxy-but-2-ynyl.

10. A compound according to claim 1 selected from:
   i) 16-demothoxy-16-(pent-2-ynyl)oxy-rapamycin
   ii) 16-demothoxy-16-(but-2-ynyl)oxy-rapamycin
   iii) 16-demothoxy-16-(propargyl)oxy-rapamycin
   iv) 16-demothoxy-16-(4-hydroxy-but-2-ynyl)oxy-rapamycin, and
   v) 16-demothoxy-40-O-(2-methoxyethyl)-16-(pent-2-ynyl)oxy-rapamycin.

11. The compound according to claim 1 which is 16-demethoxy-16-(pent-2-ynyl)oxy-rapamycin.

12. A process for making a compound of Formula I of claim 1 comprising one or more of the following steps:
   i. Reacting rapamycin or a derivative thereof with SeO$_2$ and a compound $R_1$—OH under suitable reaction conditions, wherein $R_1$ is as defined as for Formula I, or reacting rapamycin or a derivative thereof with an acid and a compound $R_1$—OH in a suitable aprotic solvent;
   ii. When the compound desired is of Formula I where $R_2$ is of Formula II and $R_3$ is other than H, reacting rapamycin or a derivative thereof with an organic radical attached to a leaving group $R_3$—Z where $R_3$ is an organic radical as defined in Formula I which is desired as the O-substituent, and Z is the leaving group in the presence of a suitable acid, or in the presence of a suitable base;
   iii. When the compound desired is of Formula I where $R_2$ is of formula III, reacting rapamycin or a derivative thereof with morpholinosulphur trifloride to obtain the aldehyde compound, then optionally oxidizing the aldehyde to the carboxylic acid or reducing the aldehyde to the corresponding alcohol; and further optionally (a) O-substituting the alcohol thus obtained, as in step ii, or (b) reacting the carboxylic acid thus obtained with an amine or alcohol in the presence of an activating or coupling reagent to give the desired amide or ester compounds respectively, or (c) condensing the aldehyde thus obtained with the desired amine or alkylenediol, respectively, under acidic conditions to obtain the iminomethyl or dioxymethylyne compounds respectively;
   iv. When the compound desired is of formula I where X is other than O, reducing a rapamycin or derivative (in O-protected form) at the 32-keto to obtain the alcohol and optionally further O-substituting as in step ii;
   v. Optionally protecting and deprotecting as necessary;
and recovering the compound of Formula I thus obtained.

13. A pharmaceutical composition comprising a compound according to claim 1 together with a pharmaceutically acceptable diluent or carrier.

14. A pharmaceutical composition comprising a compound according to claim 9 and a pharmaceutically acceptable diluent or carrier.

15. A method of treating or preventing any of the following conditions:
   (i) autoimmune disease
   (ii) acute rejection of an organ or tissue transplant
   (iii) chronic rejection of an organ or tissue transplant
   (iv) hyperacute rejection of an organ or tissue transplant
   (v) graft v. host disease transplant
   (vi) asthma
   (vii) multidrug resistance
   (viii) tumors or hyper proliferactive disorders
   (ix) fungal infections
   (x) inflammation
   (xi) infection by pathogens having Mip or Mip-like factors
comprising administering to a patient in need thereof an effective amount of a compound of claim 1.

16. A method of treating or preventing any of the following conditions:
   (i) autoimmune disease
   (ii) acute rejection of an organ or tissue transplant
   (iii) chronic rejection of an organ or tissue transplant
   (iv) hyperacute rejection of an organ or tissue transplant
   (v) graft v. host disease transplant
comprising administering to a patient in need thereof an effective amount of a compound of claim 1.

17. A method of treating or preventing any of the following conditions:
   (i) autoimmune disease
   (ii) acute rejection of an organ or tissue transplant
   (iii) chronic rejection of an organ or tissue transplant
   (iv) hyperacute rejection of an organ or tissue transplant
   (v) graft v. host disease transplant
comprising administering to a patient in need thereof an effective amount of a compound of claim 9.

18. A method of treating or preventing any of the following conditions:
  (i) autoimmune disease
  (ii) acute rejection of an organ or tissue transplant
  (iii) chronic rejection of an organ or tissue transplant
  (iv) hyperacute rejection of an organ or tissue transplant
  (v) graft v. host disease transplant comprising administering to a patient in need thereof an effective amount of a compound of claim 9 in combination with one or more of: cyclosporin, ascomycin and immunosuppressive analogs thereof; corticosteroids, cyclophosphamide, azathioprene, methotrexate, brequinar, leflunomide, mizoribine, immunosuppressive monoclonal antibodies, anti-viral drugs, and antibiotics.

19. A method of treating or preventing asthma comprising administering to a patient in need thereof an effective amount of a compound of claim 9.

\* \* \* \* \*